(12) United States Patent
Glajch et al.

(10) Patent No.: US 6,455,024 B1
(45) Date of Patent: *Sep. 24, 2002

(54) INORGANIC MATERIALS FOR RADIOACTIVE DRUG DELIVERY

(75) Inventors: Joseph L. Glajch, Nashua, NH (US); Prahlad R. Singh, Arlington, MA (US)

(73) Assignee: Bristol-Myers Squibb Pharma Company, Princeton, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/285,400

(22) Filed: Apr. 2, 1999

Related U.S. Application Data

(60) Provisional application No. 60/080,719, filed on Apr. 3, 1998.

(51) Int. Cl.[7] ............................................... A61K 51/00
(52) U.S. Cl. ..................... 424/1.33; 424/1.29; 424/1.25; 600/3
(58) Field of Search ............................... 424/1.29, 1.25, 424/1.33, 1.61; 600/1, 3, 7, 8; 252/625, 635

(56) References Cited

U.S. PATENT DOCUMENTS

| | | |
|---|---|---|
| 3,965,254 A | 6/1976 | Tofe et al. |
| 4,323,055 A | 4/1982 | Kubiatowicz et al. |
| 4,702,228 A | 10/1987 | Russell, Jr. et al. |
| 4,784,116 A | 11/1988 | Russell, Jr. et al. |
| 4,789,501 A * | 12/1988 | Day et al. .................... 252/645 |
| 4,889,707 A | 12/1989 | Day et al. |
| 5,147,631 A * | 9/1992 | Glajch et al. .............. 424/9.52 |
| 5,163,896 A | 11/1992 | Suthanthiran et al. |
| 5,405,309 A | 4/1995 | Carden et al. |
| 5,560,901 A * | 10/1996 | Brodack et al. ........... 424/1.29 |
| 5,609,850 A * | 3/1997 | Deutsch et al. .............. 424/9.5 |

FOREIGN PATENT DOCUMENTS

GB 2 024 007 1/1980

OTHER PUBLICATIONS

Anghileri, L.J., Distribution of colloidal chromic phosphate–32P in mice. Effect of particle size, Argent., Repub., Com. Nac Energ. At., CNEA, pp. 1–22, 1965.*

Abstract, Database WPI, Derwent AN: Jun. 24, 1997–382429 XP002115048 (JP(A) 9166697.

Anghileri, L.J., Distribution of colloidal chromic phosphate–32P in mice. Effect of particle size, Argent, Repub., Com. Nac Engerg. At., CNEA, pp. 1–22, 1965 (Translated).

Volkert et al. 1991, J. Nucl. Med. 32, 174–185.

Nag et al. 1995, Int. J. Radiation Oncology Biol. Phys. 31, 1, 103–107.

* cited by examiner

Primary Examiner—Michael G. Hartley
(74) Attorney, Agent, or Firm—Maureen P. O'Brien; Peter L. Dolan

(57) ABSTRACT

Radiotherapy agents which are solid or porous particles are described. The particles are of an inorganic material containing a suitable radionuclide and having an average particle diameter of about 0.05 to 5000 microns.

11 Claims, No Drawings

INORGANIC MATERIALS FOR RADIOACTIVE DRUG DELIVERY

This application claims the benefit of Provitional application Ser. No. 60/080,719, filed Apr. 3, 1998.

FIELD OF THE INVENTION

The invention relates to radiotherapy agents comprising particles of an inorganic material containing a suitable radionuclide and having an average particle diameter of about 0.05 to 5000 microns. The solid or porous inorganic particles of the present invention are administered parenterally or nonparenterally to treat a tissue or organ system. They may also be administered by direct implantation in the case of brachytherapy applications.

BACKGROUND OF THE INVENTION

The use of radionuclides for treatment of various types of cancer has been an effective alternative to other therapies, such as chemotherapy and external beam radiation. A variety of different radionuclides have been used which possess three general decay characteristics: alpha-particle emitters, beta-particle emitters, and Auger electron- and Coster-Kronig electron-emitters following electron capture. The type of radionuclide used depends on a number of factors, including the distribution of the radiation relative to the sites of tumor being targeted. The general principle is to use the radionuclidic decay to destroy cancerous cells and prevent the spread of additional cancer.

Therapeutic radionuclides have been delivered in a variety of forms. The radionuclide can be bound to a carrier molecule, such as a simple organic or inorganic ligand, a small peptide, or a monoclonal antibody and then injected intravenously for targeting to the area of desired therapy. While this approach has been effective in some cases, it relies upon the proper targeting of the ligand-radionuclide complex to the desired cancer cells, while minimizing localization in other areas of the body. Achieving this high target-to-background ratio of specificity is often difficult.

A second approach uses the principle of brachytherapy, where the radionuclide is physically applied in a more directed manner, often by direct implantation. The radionuclide is often implanted inside a container, such as a capsule or seed. Using this technique, the desired radioactivity can be spatially directed to provide the best dose to the cancerous cells, while minimizing dose to other heathly cells in the body.

Kubiatowicz, U.S. Pat. No. 4,323,055, describes the use of iodine-125 seeds incorporated in a rod-like member which is detectable by X-rays. The I-125 seeds can thus be placed in the body and located using X-ray photographs.

Russell and Coggins, U.S. Pat. No. 4,702,228, describes the use of palladium seeds containing a fraction of palladium-103 as the X-ray emitting source and methods of producing capsules containing the seeds. The use of these seeds for implantation into a tumor is also described. Russell and Coggins, U.S. Pat. No. 4,784,116, further decribes capsules and radiation-emitting materials for implantation within a living body including description of a container means for sealing the radiation-emitting material.

Day and Ehrhardt, U.S. Pat. No. 4,889,707, describes radioactive microspheres comprising a biodegradable glass material and a beta-emitting radioisotope chemically dissolved in and distributed sustantially uniformly throughout the glass material. The materials which are initially nonradioactive are subjected to neutron irradiation, thus producing a beta-emitting radioisotope. The glasses described include aluminosilicate, magnesium aluminosilicate, lithium silicate, lithium aluminosilicate, lithium aluminoborate, lithium germanate, lithium aluminogerminate, potassium silicate, potassium aluminosilicate, potassium aluminoborate, potassium germanate, and potassium aluminogermanate containing samarium-153, holmium-166, erbium-169, dysprosium-165, rhenium-186, rhenium-188, and yttrium-90. These materials are biodegradable and gradually dissolve after they are no longer radioactive.

Suthanthiran and Lakshman, U.S. Pat. No. 5,163,896, describes a pellet for a radioactive seed for use in radiation therapy where the pellet comprises a metallic substance coated with a radioactive-absorbing material of polyamino acids and radioactive material absorbed such as I-125, Pd-103, Cs-131, Cs-134, Cs-1378 (sic), Ag-111, U-235, Au-198, P-32 and C-14 and other isotopes.

Carden, U.S. Pat. No. 5,405,309, describes seeds of Pd-103 of high activity formed by bombarding an Rh target in a cyclotron with high energy particles. The seeds thus obtained are Rh containing carrier-free-Pd-103, which are then combined with a small amount of Pd and electroplated onto a pellet of electroconductive material and encapsulated within a biocompatible container or shell.

Volkert, et al., J. Nucl. Med 1991; 32:174–185, review the production and decay property considerations of therapeutic radionuclides. They summarize the characteristics needed for radiotherapeutic agents and the considerations used in choosing the appropriate materials and production schemes.

Nag, et al., Int. J. Radiation Oncology Biol. Phys., Vol. 31, No. 1, pp. 103–107, 1995 surveyed the use of brachytherapy in the United States and included a substantial list of the radioisotopes being used, the clinical applications, and their frequency of use.

SUMMARY OF THE INVENTION

This invention relates to radiotherapy agents comprising solid or porous particles of an inorganic material having an average particle diameter of about 0.05 to 5000 microns and containing a suitable radionuclide. The inorganic material includes monomeric and polymeric forms, and mixtures of monomeric and polymeric forms of one or more of the following: aluminas, carbonates, silicas, and phosphates and organic or inorganic cationic salts thereof. The inorganic material may be in a crystalline form, an amorphous form, or a mixture of crystalline and amorphous forms. The radoinuclide is coated, adsorbed, or incorporated into the matrix of the particle directly.

The inorganic particles can be prepared and fabricated using known techniques into a variety of shapes, sizes, and extents of porosity. The porous particles contain one or more pores or cavities, which may be entirely or partially enclosed by the inorganic material particle shell. For parenteral use, the particles are preferably about 0.2–10 microns in average diameter. For use in brachytherapy applications, the particles are preferably from 50 to 5000 microns in size and may be incorporated into other delivery systems, such as tubes or encapsulated seeds.

The solid or porous inorganic particles of the invention may be coated with a variety of metallic, organic or lipid materials to control the stability, pharmacokinetics, targeting, and biological effects of the particles in vivo.

The porous inorganic particles of the invention should have a density of from 30% to 100% of the density of the solid nonporous inorganic material. The pore diameter may vary depending on the size of the particles and the number of pores, to achieve the preferred density. Thus, the pore size may range from about 20 angstrom to 5000 microns. The porous nature of the particles allows for a substantial range of surface areas to be achieved, thus allowing different loadings of radioactive materials on or within the particle matrix.

The solid or porous inorganic particles of the invention can be administered parentally or nonparentally with an optional pharmaceutically acceptable carrier to a patient in need thereof, to thereby treat a tissue or organ system of that patient. They may also be administered by direct implantation in the case of brachytherapy applications.

DETAILED DESCRIPTION OF THE INVENTION

[1] In a first embodiment, the present invention provides a novel radiotherapy agent, comprising: solid or porous particles of an inorganic material having an average particle diameter of about 0.05 to 5000 microns and a suitable radionuclide.

[2] In a preferred embodiment, the present invention provides a novel radiotherapy agent, wherein:

the radionuclide is selected from: $^{89}Sr$, $^{169}Yb$, $^{32}P$, $^{33}P$, $^{90}Y$, $^{125}I$, $^{103}Pd$, $^{177}Lu$, $^{149}Pm$, $^{140}La$, $^{153}Sm$, $^{186}Re$, $^{188}Re$, $^{166}Ho$, $^{166}Dy$, $^{169}Er$, $^{165}Dy$, $^{97}Ru$, $^{193m}Pt$, $^{195m}Pt$, $^{105}Rh$, $^{67}Cu$, $^{64}Cu$, $^{111}Ag$, $^{199}Au$, $^{201}Tl$, and $^{175}Yb$; and, the inorganic material is selected from aluminas, carbonates, silicas, and phosphates, organic cationic salts thereof, inorganic cationic salts thereof, monomeric forms thereof, polymeric forms thereof, and mixtures of monomeric and polymeric forms thereof.

[3] In a more preferred embodiment, the radionuclide is distributed substantially uniformly throughout the inorganic material.

[4] In another more preferred embodiment, the radionuclide is coated onto the particle.

[5] In another more preferred embodiment, the radionuclide is adsorbed onto the particle.

[6] In another more preferred embodiment, the radionuclide is activated by neutron bombardment after formation of the particle and the radionuclide is selected from: $^{32}P$, $^{103}Pd$, $^{177}Lu$, $^{149}Pm$, $^{140}La$, $^{153}Sm$, $^{186}Re$, $^{188}Re$, $^{166}Ho$, $^{166}Dy$, $^{169}Er$, $^{165}Dy$, $^{193m}Pt$, $^{195m}Pt$, $^{105}Rh$, $^{67}Cu$, $^{64}Cu$, $^{111}Ag$, $^{199}Au$, and $^{175}Yb$.

[7] In another more preferred embodiment, the inorganic material is in a form selected from crystalline, amorphous, or a mixture of crystalline and amorphous.

[8] In another more preferred embodiment the inorganic material is a silica.

[9] In another more preferred embodiment the inorganic material is phosphate, wherein the phosphate is in a monomeric or polymeric form or a mixture of monomeric and polymeric forms.

[10] In an even more preferred embodiment the inorganic material comprises monomeric or polymeric forms, or a mixture of monomeric and polymeric forms, of one or more alkali cation phosphate salts.

[11] In a further preferred embodiment, the alkali cations are sodium, potassium, or calcium.

[12] In another more preferred embodiment the inorganic material is an alumina.

[13] In another more preferred embodiment, the particles are porous and contain an entrapped gas or liquid.

[14] In another even more preferred embodiment the entrapped gas is selected from the group: air, $O_2$, $N_2$, $H_2$, $CO_2$, He, Ne, Ar, $CF_4$, $C_2F_6$, $C_3F_8$, and $C_4F_{10}$.

[15] In another more preferred embodiment, the agent, further comprises: a pharmaceutically acceptable carrier.

[16] In another more preferred embodiment, the particle is encapsulated within a biocompatible material.

[17] In another even more preferred embodiment, the biocompatible material is selected from: titanium, aluminum, magnesium, gold, platinum, rhodium, silver, and nickel.

[18] In another even more preferred embodiment, the biocompatible material is selected from: plastic, polyvinyl chloride, polyvinyl acetate, polyethylene, polypropylene, epoxy, polyurethane, polyimide, polytetrafluoroethylene, or polyamide, polyimide, polyethylene terephthalate (PET), polytetrafluoroethylene, and polyvinylidine chloride.

[19] In another even more preferred embodiment, the biocompatible material is selected from: ethylcellulose, hydroxypropylcellulose, methylcellulose, hydroxypropylmethylcellulose, polyvinylpyrrolidine, polyethylene, glycol, albumin, gelatin, starch, collagen, dextran, modified dextrans, polylactide/polyglycolide, polyalkylcyanoacrylates, polyacrylamide, cholesterol, phosphatidylcholine, phosphatidylinositol, polysorbates, polyethlyene ethers, polyethylene esters, and polyoxyethylene/polyoxypropylene block polymers.

[20] In another more preferred embodiment, the particles are solid.

[21] In another more preferred embodiment the particles are porous and have a single pore which is entirely or partially enclosed by a shell of the inorganic material.

[22] In another even more preferred embodiment the shell thickness is 1–45% of the average particle diameter. [23] In another more preferred embodiment the particles are porous and have a plurality of pores which are entirely or partially enclosed by the inorganic material.

[24] In another more preferred embodiment the particles are porous and have a density of less than about 90% of the density of the inorganic material in a solid non-porous state.

[25] In another even more preferred embodiment the particles are porous and have a density of less than about 60% of the density of the inorganic material in a solid non-porous state.

[26] In annother further preferred embodiment the particles are porous and have a density of 0.2% to 50% of the density of the inorganic material in a solid non-porous state.

[27] In another more preferred embodiment the average particle diameter is 0.05 to 10 microns.

[28] In a second embodiment, the present invention provides a novel method of treating a tumor in a patient in need thereof, comprising: administering one of the presently claimed radiotherapy agents.

[29] In another more preferred embodiment, the agent is administered parentally,

[30] In another more preferred embodiment, the agent is administered nonparentally,

[31] In another more preferred embodiment, the agent is administered via direct implantation.

[32] In a third embodiment, the present invention provides a novel radiotherapy agent, comprising: solid or porous particles of phosphate having an average particle diameter of about 0.05 to 5000 microns and a radionuclide, wherein the radionuclide is $^{32}P$.

[33] In another preferred embodiment, the radionuclide is activated by neutron bombardment after formation of the particle.

[34] In another referred embodiment, the radionuclide is activated by neutron bombardment prior to formation of the particle.

[35] In another preferred embodiment the phosphate is in a monomeric or polymeric form or a mixture of monomeric and polymeric forms.

[36] In another even more preferred embodiment the phosphate comprises monomeric or polymeric forms, or a mixture of monomeric and polymeric forms, of one or more alkali cation phosphate salts.

[37] In a further preferred embodiment, the alkali cations are sodium, potassium, or calcium.

INORGANIC MATERIAL

The inorganic material useful in the present invention may exist in an amorphous or glass state or in a crystalline state or in a mixture of amorphous and crystalline forms. Preferably the material is in other than a glass state. The inorganic material useful in this invention includes aluminas, carbonates, bicarbonates, silicas, and phosphates in the form of monomeric salts or as polymeric or condensed forms, or as mixtures of monomeric and polymeric forms. Particles comprising mixtures of these materials are also expected to be useful in the present invention. Inorganic materials useful in the present invention include, but are not limited to, $SiO_2$, alkali salts of $CO_3^{2-}$ and $HCO_3^-$, alkali salts of $HPO_4^{2-}$, and aluminum oxides and hydroxides, such as $Al_2O_3$.

Phosphates, as the term is used herein, include various monomeric and condensed or polymeric crystalline forms and various noncrystalline or amorphous forms (including glass forms) as described in Van Wazer (1958) Phosphorus and Its Compounds, Volume 1, pp 419–770, Interscience Publishers, New York, a standard textbook in the field of phosphate chemistry. The preparation of various monomeric and condensed or polymeric forms of phosphate is appreciated by those skilled in the art of phosphate chemistry and is described in standard treatises on phosphate chemistry, for example, Van Wazer (1958) Phosphorus and Its Compounds, Volume 1, pp 419–770, Interscience Publishers, New York.

The term phosphates, as used herein, also includes derivatives of phosphates containing additional elements. For example, nitrogen can be incorporated into phosphate glasses to form oxynitride glasses, as described by Reidmeyer et al. (1986) J. Non-crystalline Solids 85: 186–203, the teaching of which is incorporated herein by reference. Nitriding the phosphate starting glass is expected to decrease the dissolution rate of the solid in water and increase the chemical stability of the solid. The preparation of phosphorus oxynitride glass by melting sodium metaphosphate in anhydrous ammonia to produce glasses containing up to 12 wt % nitrogen is described by Reidmeyer et al. Porous particles of oxynitride glasses and crystalline solids useful in the present invention can be prepared using the methods, described below.

Silicas, as used herein, includes any and all siliceous materials in the particulate form stated above. Typical silica material includes $SiO_2$. The preparation of porous silica particles is described in Bergna and Kirkland, U.S. Pat. No. 4,131,542, Kirkland, U.S. Pat. No. 3,782,075, and Kirkland, U.S. Pat. No. 3,505,785, the contents of which are incorporated herein by reference.

Radionuclides

The radionuclide to be used in the presently claimed invention is selected from the group: $^{89}Sr$, $^{169}Yb$, $^{32}P$, $^{33}P$, $^{90}Y$, $^{192}Ir$, $^{125}I$, $^{131}I$, $^{103}Pd$, $^{177}Lu$, $^{149}Pm$, $^{140}La$, $^{153}Sm$, $^{186}Re$, $^{188}Re$, $^{166}Ho$, $^{166}Dy$, $^{137}Cs$, $^{57}Co$, $^{169}Er$, $^{165}Dy$, $^{97}Ru$, $^{193m}Pt$, $^{195m}Pt$, $^{105}Rh$, $^{68}Ni$, $^{67}Cu$, $^{64}Cu$, $^{109}Cd$, $^{111}Ag$, $^{198}Au$, $^{199}Au$, $^{201}Tl$, $^{175}Yb$, $^{47}Sc$, $^{159}Gd$, $^{212}Bi$, and $^{77}As$.

Preferably the radionuclide is selected from the group: $^{89}Sr$, $^{169}Yb$, $^{32}P$, $^{33}P$, $^{90}Y$, $^{125}I$, $^{103}Pd$, $^{177}Lu$, $^{149}pm$, $^{140}La$, $^{153}Sm$, $^{186}Re$, $^{188}Re$, $^{166}Ho$, $^{166}Dy$, $^{169}Er$, $^{165}Dy$, $^{97}Ru$, $^{193m}Pt$, $^{195m}Pt$, $^{105}Rh$, $^{67}Cu$, $^{64}Cu$, $^{111}Ag$, $^{199}Au$, $^{201}Tl$, and $^{175}Yb$.

Materials which are initially nonradioactive can be subjected to neutron irradiation, thus producing a beta-emitting radioisotope. Neutron irradiation is achieved by encapsulating the material in high purity quartz vials and placing these vials in a neutron flux that could be in the range of $1\times10^{13}$ to $5\times10^{15}$ n.s-1.cm-2 (depending on the flux of the reactor). Irradiation times typically range up to halfsaturation and are also dependent on the flux, cross-section of the target and its natural abundance.

The amount of radionuclide present in terms of wt % will depend on a number of issues: radionuclide chosen, its physical properties (T1/2, energy), method of delivery, and amount of activity required. Typically the latter will dictate the wt % of the radionuclide. A simple empirical formula developed by Memorial Sloan-Kettering Cancer Center is routinely used to calculate activity required to treat a given tumor volume. This is generally calculated by the "dimension averaging" technique. Total millicuries of the radioactivity implanted is determined by multiplying the average of the three mutually perpendicular implant dimensions d(a) by an appropriate factor (dependent on the isotope). Typically the desired dose range is at least 450 Gy/d(a) at <3.0 cm and at least 150 Gy at >3.0 cm. The average implant dimension is $d(a)=(a+b+c)/3$.

Particles

The inorganic particles of the invention have the advantages of good mechanical stability and rigidity, which are important attributes in the synthesis and subsequent handling of these particles for radionuclide drug delivery. In addition, inorganic particles can be prepared and fabricated, using known techniques, into a variety of shapes, sizes, and extents of porosity, in order to obtain the most desirable therapeutic effects. In addition, inorganic porous particles can be prepared with a range of different solubilities in aqueous solution, such as a body fluid. The solubility of the inorganic porous particle may affect the rate of biodegradation and clearance of the agent in vivo and may, thereby, be an important property affecting the biological responses and toxicity associated with the therapeutic agent and its subsequent elimination from the body after treatment has occurred.

The inorganic porous particles useful in the present invention may comprise an inorganic solid material that encloses or partially encloses one or more pores or cavities. The porous particles of the invention may contain an entrapped gas or liquid to provide a suitable echogenic interface to enhance an ultrasound image, which could be useful for directing the placement of the therapeutic agent and determining the dose delivered. The pore or pores may be completely enclosed or encapsulated by the inorganic material or may be partially enclosed and open to the surface of the particle. Thus, the particles are porous or hollow and contain an entrapped or partially entrapped gas or liquid in the pore or pores. Porous inorganic particles useful in this invention include particles having a single pore enclosed by a solid shell; i.e., hollow particles. Alternatively, the porous particle may have a single pore which is partially enclosed by a solid shell. The porous particles of the invention also include particles containing a plurality of pores. The pores may be interconnected and may connect to an opening at the surface of the particle. The particles may also contain pores which are completely enclosed and are not interconnected or open to the surface of the particle. Particles with noninterconnected and completely enclosed pores are known as closed cell foam type particles.

The nonporous or solid inorganic particles useful in the present invention should have a density of essentially 100% of the density of the solid inorganic material. These particles should be comprised of the inorganic material in a particle form which is substantially free of any pores, voids, or other cavities. This nonporous structure would permit the radionuclide to be coated or sorbed on the outside of the surface of the particle or incorporated completely or partially throughout the matrix of the particle.

The inorganic particles useful in the present invention may range in size and shape or morphology. A variety of particle shapes are useful in the present invention. For example, the particles may range from roughly spherical shapes to rod-like shapes and may be regular or irregular in shape. The particle size, measured as the average particle diameter, should be in the range of about 0.05 to 5000 microns. For irregularly shaped particles, the term average particle diameter refers to the effective particle diameter or Stokes diameter of the particle. For injection or parenteral administration, the particles are preferably about 0.2–10 microns in diameter. For non-parenteral administration, such as ingestion or directed application in brachytherapy, larger particles may be acceptable or preferred.

For purposes of tissue perfusion, the porous inorganic particle should preferably be about 0.2–10 microns in diameter and thereby small enough to pass through capillaries, which are about 8 to 10 microns in diameter, so as to perfuse the tissue. The porous inorganic particles of the invention should be small enough to permit their passage through capillaries without being filtered out and capable of perfusing the tissue and produce an enhanced ultrasound image that is of resolution sufficient to distinguish, for example, between well perfused and poorly perfused tissue.

The porous gas-containing inorganic particles of the invention should have a density that is less than about 90% of the density of the solid solid inorganic material, and preferably are less than 60% of the density of the solid solid inorganic material. The density of the gas-containing porous inorganic particles of the invention is preferably about 0.2–50% of the density of the non-porous inorganic material. The pore diameter may vary depending on the size of the particle and the number of pores, to achieve the preferred particle density. Thus, the pore size may range from about 20 angstroms to 500 microns. The pore diameters may be in the range of about 20 to 2000 angstroms for porous particles having a plurality of pores. For porous particles having a single pore, the thickness of the solid shell may vary. The shell thickness may be about 1–45% of the diameter of the particle. Thus, for porous particles having a single pore (i.e., hollow particles) ranging in particle size from about 0.2 to 500 microns, the pore size may correspondingly vary from about 0.2 to 500 microns.

The porous inorganic particles typically have a specific surface area of about 1 to 1500 $m^2/g$. The porous inorganic particles of the invention may have a gas volume per gram of particle of greater than 0.05 mL/g, and preferably in the range of about 0.05 to 50 mL/g.

Porous inorganic particles of the invention may be prepared using standard methods for the preparation of porous particles. For example, porous inorganic particles may be prepared using standard methods involving the spraying of a metal salt solution into a furnace at elevated temperatures, such as standard spray drying, evaporation decomposition, high temperature aerosol decomposition, or drop-generator procedures (see below).

The spray-drying procedure, as applied for the preparation of porous silica particles is described in Bergna and Kirkland, U.S. Pat. No. 4,131,542, the teaching of which is incorporated herein by reference. Similar procedures can be used for the preparation of porous particles composed of other materials including carbonates, aluminates, phosphates, and mixtures thereof.

The drop-generator process for preparing high precision glass spheres is described by Hedricks (1984) Glass Science and Technology, volume 2, pp 149–168, (ed. Uhlmann and Kreidl) Academic Press, the teaching of which is incorporated herein by reference.

The high temperature aerosol decomposition (HTAD) process is described by Moser and Lennhoff (1989) Chem. Eng. Comm. 83: 241–259, the teaching of which is incorporated herein by reference. This procedure involves the spraying of a metal salt solution into a tube furnace at elevated temperatures, resulting in solvent evaporation, salt decomposition, and metal oxide ceramic particle formation. The HTAD of Moser and Lennhoff may be used for the synthesis of metal oxide particles having a range of surface areas and a range of particle morphologies, from nearly perfect hollow spheres to fragmented particles. By controlling the HTAD reactor conditions, materials having the desired morphology (spheres or fragmented particles), high or low surface area, phase purity, compositional purity, pore size distribution, and aqueous solubility may be obtained.

Hollow inorganic particles (i.e., particles having a single pore) may also be prepared by the process of coating a template or core particle composed of a material, such as polystyrene latex, with the inorganic material to form a shell around the core particle, and then subsequently removing the template or core material. Removal of the core can be achieved, for example, by heating and calcination of the core material. In such a process, the inorganic particle size, pore size, and thickness of the inorganic shell can be controlled quite precisely. Such a process of preparing hollow spherical particles is described by Kawahashi and Matijevic (1990) J. of Colloid and Interface Science 143:103–110.

The gas in the pore or pores of the porous inorganic particle may be a pure gas or mixture of gases, such as air. For example, elemental gases such as $O_2$, $N_2$, $H_2$, He, argon, and other noble gases, and other light gases, such as $CO_2$, $CF_4$, or $C_2F_6$, $C_3F_8$, $C_4F_{10}$, and other fluorocarbon gases are expected to provide useful ultrasound contrast properties. The gases may be incorporated into the pores of the particles, for example, by exchange at high temperature and/or high pressure. Preferably the perfluorocarbon have less than six carbon atoms, e.g., $CF_4$, $C_2F_6$, $C_3F_8$, cyclo-$C_4F_8$, $C_4F_{10}$, $C_5F_{12}$, cyclo-$C_5F_{10}$, cyclo-$C_4F_7$ (1-trifluoromethyl), propane(2-trifluoromethyl)-1,1,1,3,3,3 hexafluoro, and butane(2-trifluoromethyl)-1,1,1,3,3,3,4,4,4 nonafluoro. Also preferred are the corresponding unsaturated versions of the above compounds for example $C_2F_4$, $C_3F_6$, the isomers of $C_4F_8$. The halogenated versions of hydrocarbons, where other halogens are used to replace F (e.g., Cl, Br, I) would also be useful, but may not be as desirable as the perfluorinated versions. Also, mixtures of these gases, especially mixtures of perfluorocarbons with other perfluorocarbons and mixtures of perfluorocarbons with other inert gases, such as air, $N_2$, $O_2$, He, would be useful.

The porous inorganic particles useful in the present invention may have a range of solubility in aqueous solution. Porous inorganic particles of any desired solubility can be obtained in several ways. The solubility can be controlled by selection of the desired particle surface area, the particle shell thickness, and/or the type of solid used in the particle. For example, as discussed below, the solubility of phosphate materials can be controlled by the temperature and heating time used to prepare various amorphous or crystalline forms of phosphate material.

The porous inorganic particles must have a sufficiently slow dissolution rate in aqueous solution so as to exist in vivo following administration for at least about 1–30 minutes to provide enough time for the therapeutic radionuclide decay to occur. For certain imaging applications, such as cardiovascular applications, where the therapeutic agent is administered parenterally, it may be desirable to use particles which are relatively soluble in serum or other body fluid. Porous inorganic particles having slower dissolution rates (reduced solubility) or insoluble particles, such as silica or alumina particles, may be desired for other uses, such as longer radnuclide half-life isotopes. These particles could have dissolution half-lives as long as months.

The radionuclide of interest may be contacted with the particle by a variety of techniques, including precipitation, co-precipitation, chemisorption, physical sorption, and vapor deposition. The preferred technique would be dependent on radionuclide and particle type used, but in general, co-precipiation would be preferred for incorporation of radionuclide as a part of the particle throughout the matrix, chemisorption or physical sorption would be preferred for coating the outside of a particle or coating all or some of the pores (especially physical sorption).

Precipitation is the process wherein a solution containing the desired cation is mixed with a solution containing an anion. As example, a solution of barium chloride is mixed with a solution of sodium sulfate (or sodium phosphate) to give a precipitate of barium sulfate (or barium phosphate).

Physical sorption or physisorption is the process of adsorption of radionuclides on a surface through solely physical interaction such as van der Waals forces.

Absorption (or adsorption) is the process where a solid, insoluble material takes another substance initially in solution onto its surface. This may occur by physical absorption or by exchange of ions.

Chemisorption is the adsorption of radionuclides on a surface through the formation of a chemical bond between the radionuclide and the surface.

Vapor deposition is the process wherein a material (usually a metal) is transported through the gas phase and allowed to impinge on a solid surface and be thereby deposited. The metal is brought into the vapor phase by strong heating generally in a high vacuum. Sputtering is a variant where the pressure may be higher. Chemical vapor deposition is another variation wherein the radionuclide to be deposited (again generally a metal) is first incorporated into a volatilisable composition and as a result of heating that substance liberates the desired metal which condenses on the surface and at least one chemical bond is formed between the radionuclide and the surface.

Co-precipitation is the process in which the radionuclide in a soluble form is intimately mixed with a soluble precursor of the inorganic material. The radionuclide and the inorganic materials are made to concurrently precipitate by means of changing the solvent, adding a precipitating solvent in which the radionuclide and inorganic materiols are not soluble, changing the temperature, or changing the pH.

The porous or solid inorganic particles of the present invention may be directly planted or administered with an acceptable carrier to a person to direct the therapy to the tissue or organ system that is being treated. Thus, the inorganic particles must have acceptable biocompatibility and toxicity properties in humans. The biocompatibility criteria will depend in part on the type of therapy and area of administration or direct transplantation. For example, the biocompatibility criteria may be different for gastrointestinal administration than for parenteral administration of the therapeutic agent.

Physiologically acceptable pharmaceutical carrier fluids may be used to transport and preferably stabilize the suspension of the particles (prevent sedimentation), and retard the dissolution of the particles. Useful carrier fluids include, but are not limited to: water; aqueous solutions of one or more physiologically acceptable inorganic salts, such as physiological buffered solutions; aqueous solutions of mono- or disaccharides, such as galactose and lactose; and physiologically acceptable monofunctional or polyfunctional alcohols or their aqueous solutions. Also included are carrier fluids which enhance the adherence of the contrast agent to the organ or tissue walls or surface. Suitable pharmaceutical carriers are described in Remington's Pharmaceutical Sciences, Mack Publishing Co., a standard reference text in this field.

Biocompatiable Material

The porous or solid inorganic particles of the invention optionally may be coated with a biocompatible material, such as those described below, to control the stability, pharmacokinetics, targeting, and biological effects of the particles in vivo. Coating or microencapsulation of the particles can be used to enhance their stability in the formulation, to prevent aggregation, to alter their tissue distribution in the body and their elimination from the body, to reduce toxicity or enhance effectiveness, to reduce the adherence of biological materials which trigger immune reactions or thromboembolic reactions, to control the dissolution rate of soluble particles, and to control the permeation of water and other substances into and out of the particle matrix, among other uses.

Methods for coating solid particles are described by J. Bakan in The Theory and Practice of Industrial Pharmacy (L. Lachman, H. A. Lieberman, and J. L. Kanig, eds.) pp 419–429. The methods generally most useful for coating particles less than 100 microns approximate size include air suspension, coacervation-phase separation, multiorifice centrifugal, and solvent evaporation. The coating might vary in composition, thickness, and porosity, depending on the intended effect.

The purpose of encapsulating the particles is to prevent leakage of the source into the patient. The thickness of the biocompatible material layer will depend upon the material chosen. One of ordinary skill in the art would recognize that the layer would need to be of sufficient thickness to prevent leakage of the source if the device is exposed to body fluids.

Biocompatible, as used herein, is intended to indicate a material which is medically acceptable to be placed within a patient for a sufficient length of time to affect brachytherapy treatment. A biocompatible capsule, as may be used herein is a sealed tube encapsulating (i.e., housing) the particle(s). It is preferred that the capsule have an open end and a closed end. The capsule is preferably sealed with a suitable end cap using mechanical techniques such as swaging or laser/electron beam welding or by using an equally impervious sealing agent, adhesive, glue or similar sealant.

Representative organic materials to form the biocompatible coating include organic polymeric substances including cellulose polymers such as ethylcellulose, hydroxypropylcellulose, methylcellulose, and hydroxypropylmethylcellulose, polyvinylpyrrolidone, polyethylene glycol, albumin, gelatin, starch, collagen, dextran and modified dextrans, polylactide/polyglycolide, polyalkylcyanoacrylates, polyacrylamide, lipids such as cholesterol, phosphatidylcholine, and phosphatidylinositol, and surfactants such as polysorbates, polyethylene ethers and esters, and polyoxyethylene/polyoxypropylene block polymers. The inorganic particles of the invention may also optionally be coated with a surface-active substance, such as those described by Hilman et al., European Patent Application Publication Number 122,624. Many of these coatings will also be useful for the attachment of targeting ligands through coating, adsorbing, covalent, or non-covalent bonding.

Another example of a biocompatible material is a thin coating of titanium, aluminum, magnesium, gold, platinum, rhodium, silver or any of the noble metals, including alloys such as gold-platinum, platinum-rhodium, platinum-iridium and similar durable coatings used in the jewelry industry.

Further examples of biocompatible materials are thermoplastic polymer coatings such as polyvinyl chloride, polyvinyl acetate, polyethylene, polypropylene, or any other medical grade polymer resistant to radiation, and applied through a hot dip or coating process. These polymeric coatings can be air or catalytically cured.

Still another example of a biocompatible material is a thermoset polymer coating such as epoxy, polyurethane, polyimide, polytetrafluoroethylene (e.g., Teflon®), or polyamide (e.g., Nylon®), or any other medical grade thermoset polymers resistant to radiation, preferably, a polyimide. Coatings of this type can be cured by heating, ultraviolet light, using a catalyst, or using chemical hardeners. Materials such as polyethylene terephthalate (PET), polytetrafluoroethylene, polyvinylidine chloride, or other types of heat shrink tubing may also be applied to the particles.

For use in brachytherapy applications, the particles are preferably from 50 to 5000 microns in size and may be incorporated into other delivery systems, such as tubes and encapsulated seeds. Description of various delivery systems useful for brachytherapy can be found in Nag, ed. Principles and Practice of Brachytherapy, Futura Publishing Co., 1997.

Other features of the invention will become apparent in the course of the following descriptions of exemplary embodiments which are given for illustration of the invention and are not intended to be limiting thereof.

EXAMPLES

Example 1
Preparation of Solid Radiolabelled Phosphate Particles of Varying Solubility An aqueous solution of disodium dihydrogen pyrophosphate$^{33}$P is prepared by dissolving 8 g of the anhydrous salt in water and making up to 100 mL. 50 mL of this solution is nebulized into 900 mL of methyl alcohol using a Sono-Tek ultrasonic nozzle (Model # S/N 12096), operated under the manufacturers recommended conditions. After the salt particles have settled, the aqueous methanol is decanted. To the damp particles is added 400 mL of dry methanol; the suspension is stirred and filtered using a fine glass filter. The particles are washed with about 100 mL of dry methanol and dried over calcium chloride dessicant, which adsorbs alcohol, as well as water.

Samples of the dry particles, which consist of crystalline spheroids of sodium pyrophosphate$^{33}$P hexahydrate of about 3 microns in diameter, are then heated at various temperatures from 200° C. to 400° C. for various times from 2 to 7 hr. When the particles are prepared by heating at 300° C. or greater, for longer than 2 hr, the particles become largely insoluble. When particles are prepared by heating at intermediate temperatures, in the range of about 250° to 275° C., phosphate particles are prepared having varying solubility (i.e., varying dissolution rates) in the range between the extremes of rapid dissolution and insolubility.

Example 2
Preparation of Solid calcium and Sodium Radiolabelled Phosphate Particles of Varying Solubility Powdered calcium metaphosphate, $Ca(PO_3)_2$, (27.6 g) and 29.8 g sodium dihydrogen phosphate$^{33}$P, $NaH_2{}^{33}PO_4 \cdot H_2O$, are mixed and heated in a platinum dish to 1000° C. The moderately viscous liquid is poured onto a cold steel plate to give a clear glass. This is ground up and sieved to give a particle size of about 100 microns. This composition corresponds to an intimate mixture of $Ca(PO_3)_2$ and $NaPO_3$ in a molar ratio of Ca:Na of 1:2.

By using appropriate other ratios of starting ingredients there can be prepared other glasses of calcium-sodium metaphophte in the molar ratios of Ca:Na of 1:4, 1:10, and 1:20.

The rate of dissolution in water is dependent on the ratio of Ca:Na. Higher ratios of Ca:Na result in essentially insoluble particles, while lower ratios dissolve in minutes.

Example 3
Preparation of Calcium Carbonate Particles Coated with $^{169}$Yb $CaCl_2$ (1M, 1000 mL) is poured rapidly into 950 mL of 1 M $Na_2CO_3$ with stirring. To decrease the formation of calcite, 1 g of polyvinylpyrrolidone or polyvinyl alcohol is added. After one minute the mixture is filtered, washed, air dried, and dried at 160° C. Vaterite spheres of 2–3 $\mu$m in size can be prepared in this manner. When the $CaCl_2$ and $Na_2CO_3$ solutions are 0.5 M, the resulting particles are expected to be approximately 15 $\mu$m in size; when the solutions are 0.2 M, the particles are expected to be 25 $\mu$m in size.

5 g of the resulting particles are placed in a solution containing $^{169}$YbNO$_3$ dissolved in 1.0 mL of distilled water and then reacted with a 2 mL solution of NaBH$_4$ solution in 0.2 N NaOH resulting in precipitation. The resulting precipitate is treated in an ultrasonic bath for 2 min and then centrifuged for 2 min. After decantation of the supernatant the remaining solid is washed with distilled water or 0.9% NaCl to remove residual NaBH$_4$ and leave a coating of $^{169}$Yr on the CaCO$_3$ particles.

Example 4
Preparation of Calcium-$^{99}$Strontium Carbonate Particles 1000 mL of 0.9M $CaCl_2$ and 0.1M $^{90}SrCl_2$ is poured rapidly into 950 mL of 1M $Na_2CO_3$ and with stirring. To decrease the formation of calcite, 1 g of polyvinylpyrrolidone or polyvinyl alcohol is added. After one minute the mixture is filtered, washed, air dried, and dried at 160° C. Spheres of 2–3 $\mu$m in size containing a mixture of CaCO$_3$ and $^{90}$SrCO$_3$ can be prepared in this manner. When the $CaCl_2/^{90}SrCl_2$ and $Na_2CO_3$ solutions are 0.5 M, the resulting particles are expected to be approximately 15 $\mu$m in size; when the solutions are 0.2 M, the particles are expected to be 25 $\mu$m in size.

Example 5
Preparation of Solid Phosphate Particles of Varying Solubility and Activation in a Nuclear Reactor An aqueous solution of disodium dihydrogen pyrophosphate was prepared by dissolving 8 g of the anhydrous salt in water and making up to 100 mL. 50 mL of this solution was nebulized into 900 mL of methyl alcohol using a Sono-Tek ultrasonic nozzle (Model # S/N 12096), operated under the manufacturers recommended conditions. After the salt particles had settled, the aqueous methanol was decanted. To the damp particles was added 400 mL of dry methanol; the suspension was stirred and filtered using a fine glass filter. The particles were washed with about 100 mL of dry methanol and dried over calcium chloride dessicant, which adsorbs alcohol, as well as water.

The particles obtained in this manner can then be stored for long periods of time. When needed, these can be activated in a nuclear reactor to produce $^{32}$P-containing particles Obviously, numerous modifications and variations of the present invention are possible in light of the above teachings. It is therefore to be understood that within the scope of the appended claims, the invention may be practiced otherwise that as specifically described herein.

What is claimed is:

1. A non-porous solid particle radiotherapy agent, comprising:
   inorganic material having an average particle diameter of about 0.05 to 5000 microns and a suitable radionuclide, wherein:
   the inorganic material is an alkali cation salt of $HPO_4^{2-}$, monomeric forms thereof, polymeric forms thereof and mixtures of monomeric and polymeric forms thereof;
   the radionuclide being distributed substantially uniformly throughout the inorganic material;
   the radionuclide being activated by neutron bombardment after formation of the particle; and
   wherein the dissolution rate of the particle is about 1 to 30 minutes following administration to a patient.

2. A radiotherapy agent according to claim 1, wherein the radionuclide is selected from: $^{32}$P, $^{103}$Pd, $^{177}$Lu, $^{149}$Pm, $^{140}$La, $^{153}$Sm, $^{186}$Re, $^{188}$Re, $^{166}$Ho, $^{166}$Dy, $^{169}$Er, $^{165}$Dy, $^{193m}$Pt, $^{195m}$Pt, $^{105}$Rh, $^{67}$Cu, $^{64}$Cu, $^{111}$Ag, $^{199}$Au, and $^{175}$Yb.

3. A radiotherapy agent according to claim 1, wherein the inorganic material is in a form selected from crystalline, amorphous, or a mixture of crystalline and amorphous.

4. A radiotherapy agent according to claim 1, wherein the alkali cation is sodium, potassium, or calcium.

5. A radiotherapy agent according to claim 1, wherein the agent, further comprises: a pharmaceutically acceptable carrier.

6. A radiotherapy agent according to claim 1, wherein the average particle diameter is 0.05 to 10 microns.

7. A radiotherapy agent, according to claim 1, wherein the radionuclide is $^{32}$P.

8. A method of treating a tumor in a patient in need thereof, comprising:
   administering a therepeutically effective amount of a radiotherapy agent of claim 1.

9. A method according to claim 8, wherein the agent is administered parentally.

10. A method according to claim 8, wherein the agent is administered nonparentally.

11. A method according to claim 8, wherein the agent is administered via direct implantation.

* * * * *